United States Patent [19]

Sybert et al.

[11] Patent Number: 5,756,781

[45] Date of Patent: May 26, 1998

[54] METHOD FOR MAKING TRIS (HYDROXYPHENYL) COMPOUNDS USING ION EXCHANGE

[75] Inventors: Paul Dean Sybert; Gaylord Michael Kissinger, both of Evansville, Ind.; Ashok Kumar Mendiratta, Arlington Heights, Ill.

[73] Assignee: General Electric Company, Pittsfield, Mass.

[21] Appl. No.: 536,575

[22] Filed: Sep. 29, 1995

[51] Int. Cl.$^6$ .................................................. C09B 11/04
[52] U.S. Cl. ........................ 552/115; 525/462; 528/198; 528/371
[58] Field of Search .................... 552/115; 525/462; 528/371, 198

[56] References Cited

U.S. PATENT DOCUMENTS

| | | |
|---|---|---|
| 2,789,143 | 4/1957 | Arnold et al. . |
| 3,049,568 | 8/1962 | Apel et al. . |
| 3,049,569 | 8/1962 | Apel et al. . |
| 3,153,001 | 10/1964 | Apel et al. . |
| 3,172,916 | 3/1965 | Wagner . |
| 3,221,061 | 11/1965 | Grover et al. . |
| 3,394,089 | 7/1968 | McNutt et al. . |
| 3,544,514 | 12/1970 | Schnell et al. . |
| 3,579,542 | 5/1971 | Meyer et al. . |
| 3,644,538 | 2/1972 | Starnes, Jr. . |
| 3,692,914 | 9/1972 | Meyer et al. . |
| 3,969,421 | 7/1976 | d'Ostrowick et al. . |
| 4,113,879 | 9/1978 | Jones et al. . |
| 4,201,878 | 5/1980 | Mark et al. . |
| 4,294,995 | 10/1981 | Faler et al. . |
| 4,317,944 | 3/1982 | Davis . |
| 4,337,369 | 6/1982 | Vanderpool et al. . |
| 4,375,567 | 3/1983 | Faler . |
| 4,385,191 | 5/1983 | Petrille et al. . |
| 4,391,997 | 7/1983 | Mendiratta . |
| 4,394,496 | 7/1983 | Schrader . |
| 4,396,728 | 8/1983 | Faler . |
| 4,400,555 | 8/1983 | Mendiratta . |
| 4,478,956 | 10/1984 | Maki et al. . |
| 4,507,509 | 3/1985 | Mendiratta . |
| 4,514,334 | 4/1985 | Mark .................................. 552/115 X |
| 4,584,416 | 4/1986 | Pressman et al. . |
| 4,590,303 | 5/1986 | Mendiratta . |
| 4,599,463 | 7/1986 | Mark . |
| 4,695,408 | 9/1987 | Chang .................................. 552/115 |
| 4,754,081 | 6/1988 | Mott . |
| 4,812,575 | 3/1989 | Vogl et al. . |
| 4,835,284 | 5/1989 | Seino . |
| 4,845,180 | 7/1989 | Henry et al. . |
| 4,847,432 | 7/1989 | Faler . |
| 4,888,400 | 12/1989 | Boden et al. . |
| 4,943,637 | 7/1990 | Seino et al. . |
| 4,992,598 | 2/1991 | Strutz et al. . |
| 5,021,521 | 6/1991 | Krabbenhoft et al. . |
| 5,068,285 | 11/1991 | Laughner . |
| 5,087,663 | 2/1992 | Laughner . |
| 5,097,008 | 3/1992 | Krabbenhoft et al. . |
| 5,099,027 | 3/1992 | Vogl et al. . |
| 5,130,467 | 7/1992 | Mott et al. . |
| 5,136,110 | 8/1992 | Walters et al. . |
| 5,191,038 | 3/1993 | Krabbenhoft et al. . |
| 5,202,505 | 4/1993 | Murphy et al. . |
| 5,215,856 | 6/1993 | Jayaraman . |
| 5,243,018 | 9/1993 | Kuze et al. . |
| 5,274,069 | 12/1993 | Vircari et al. . |
| 5,300,559 | 4/1994 | Sheehan et al. . |
| 5,300,589 | 4/1994 | Sheehan et al. . |
| 5,300,698 | 4/1994 | Asiam et al. . |
| 5,312,988 | 5/1994 | Sheehan et al. . |
| 5,354,907 | 10/1994 | Sheehan et al. . |
| 5,362,843 | 11/1994 | Vicari et al. . |
| 5,367,044 | 11/1994 | Rosenquist . |
| 5,438,142 | 8/1995 | Fritsch et al. . |

FOREIGN PATENT DOCUMENTS

| | | |
|---|---|---|
| 0031302 | 7/1981 | European Pat. Off. . |
| 56-115733 | 9/1981 | Japan . |
| 57-142936 | 9/1982 | Japan . |
| 57-159733 | 10/1982 | Japan . |
| 2071090 | 9/1981 | United Kingdom . |

*Primary Examiner*—Paul F. Shaver

[57] ABSTRACT

An improved method for the preparation of tris(4-hydroxyphenyl) compounds is provided. In particular, an improved method for preparing 1, 1,1-tris(4'-hydroxyphenyl)ethane is provided which comprises heating a mixture comprising phenol and 4-hydroxy acetophenone in the presence of effective amounts of an ion exchange catalyst and a mercaptan as a copromoter such that the resulting 1,1,1-tris(4'-hydroxyphenyl)ethane is substantially free of various reaction impurities.

17 Claims, No Drawings

METHOD FOR MAKING TRIS (HYDROXYPHENYL) COMPOUNDS USING ION EXCHANGE

BACKGROUND OF THE INVENTION

This invention relates to an improved process for making tris(hydroxyphenyl) compounds using ion exchange resins. More particularly, this invention relates to the preparation of 1,1,1-tris(4'-hydroxyphenyl)ethane that is substantially free of various impurities from phenol and 4-hydroxyacetophenone.

The condensation of phenol and 4-hydroxyacetophenone into 1,1,1-tris(4'-hydroxyphenyl)ethane (hereafter referred to as THPE) has generally been accomplished using mineral acids as catalysts. Examples of these reaction can be found in U.S. Pat. Nos. 3,579,542 (Meyer et al), 3,692,914 (Meyer et al), and 4,992,598 (Strutz, et al.). These preparation conditions typically require extended reaction times and lead to substantial amounts of various side products and relatively low yields of THPE.

THPE, having the general chemical structure as shown in Formula (I):

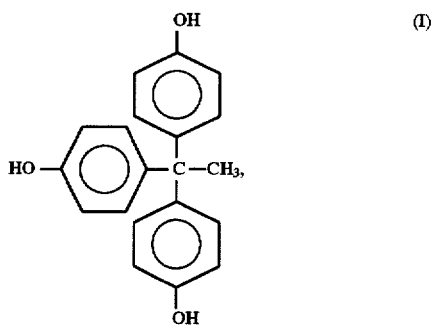

is used as a hardener for epoxy resins and as a branching agent in thermoplastic resins, such as polycarbonate and polyester resins. As such, it is important that the material be pure and free of various possible isomers and impurities in order to fully obtain the desired properties in the final product. Recrystallization techniques have been developed for purifying THPE but are not quantitative for material recovery from the reaction mixture. An example of a crystallization technique for THPE can be found in U.S. Pat. No. 4,992,598 (Strutz, et al).

Other condensation reactions, for example, the conversion of various phenols and ketones into bis-phenols, have been accomplished with mineral acids or ion exchange resins as catalysts. In these condensation reactions for the production of bis-phenols using acids or ion exchange resins, elimination of the water by-product from the reaction mixture is not critical and conversions in excess of 90% to the desired bis-phenol are typical without removal of the water of reaction. Such reactions for the preparation of bis-phenols can be found in U.S. Pat. Nos. 3,049,568, 3,049,569 and 3,153,001 (Apel, et al) and 3,221,061 (Grover), among other references. During the condensation reactions for the production of bis-phenols using ion exchange resins, significant amounts of isomeric impurities, in addition to other unidentified impurities, are formed. As a result of the formation of undesirable contaminants, extensive efforts also have to be taken to purify the desired reaction product from the reaction mixture before it can be used in various polymerization reactions. The use of ion exchange catalysts for the preparation of tris-(hydroxyphenyl) compounds, for example THPE, is unknown.

Due to the costs and efforts associated with the conversion and subsequent purification of tris-(hydroxyphenyl) compounds and in particular THPE prepared using mineral acids to catalyze the condensation reactions, it is apparent that a need exists for improved methods for the preparation of these materials.

SUMMARY OF THE INVENTION

The long felt needs set forth above have now been satisfied by the important discovery of an improved process for the preparation of tris-(hydroxyphenyl) compounds which comprises heating a mixture comprising phenols and 4-hydroxyacetophenones in the presence of an ion exchange catalyst and a mercaptan as a copromoter. These reactions result in the preparation of the desired tris(hydroxyphenyl) compounds that is substantially free of impurities, in sharp contrast to traditional ion-exchange catalyzed condensations used to prepare bis-phenols as discussed above.

The above mentioned process can be further improved by heating the reaction mixture in the presence of the catalyst with removal of the water of reaction from the reaction mixture. These processes result in the preparation of the desired tris(hydroxyphenyl) compounds with an increased rate of conversion and improved yields over condensation reactions wherein the water of reaction is not removed.

In a preferred embodiment of the invention, THPE can be produced, that is substantially free of impurities, from phenol and 4-hydroxyacetophenone.

The descriptions which follow provide further details regarding the invention.

DETAILED DESCRIPTION OF THE INVENTION

There is provided by the present invention a method for the preparation of tris(hydroxylphenyl) compounds, and in particular THPE, the method of which comprises heating a mixture of, for example, phenol and 4-hydroxyacetophenone in the presence of effective amounts of an ion exchange catalyst and at least one mercaptan as a copromoter.

There is also provided by this invention a method for the preparation of THPE which comprises heating a mixture of phenol and 4-hydroxyacetophenone in the presence of effective amounts of an ion exchange catalyst and at least one mercaptan as a copromoter such that the resulting THPE is substantially free of various reaction impurities.

There is also provided by this invention a method for the preparation of THPE which comprises heating a mixture of phenol and 4-hydroxyacetophenone in the presence of effective amounts of an ion exchange catalyst and at least one mercaptan as a copromoter such that the resulting THPE is substantially free of various reaction impurities, even at low conversions of the 4-hydroxyacetophenone.

There is also provided by the present invention a method for the preparation of THPE which comprises heating a mixture of phenol and 4-hydroxyacetophenone in the presence of effective amounts of an ion exchange catalyst and at least one mercaptan that is polymer bound as a copromoter.

There is also provided by the present invention a method for the preparation of THPE which comprises heating a mixture of phenol and 4-hydroxyacetophenone in the presence of an effective amount of a catalyst with the removal of the water of reaction from the reaction mixture.

There is also provided by this invention a method for the preparation of THPE which comprises heating a mixture of phenol and 4-hydroxyacetophenone in the presence of an effective amount of an acid catalyst with removal of the water of reaction from the reaction mixture.

There is also provided by this invention a method for the preparation of THPE which comprises heating a mixture of phenol and 4-hydroxyacetophenone in the presence of effective amounts of an ion exchange catalyst and at least one mercaptan as a copromoter with removal of the water of reaction from the reaction mixture.

Various ortho and meta- substituted phenol species of Formula (II):

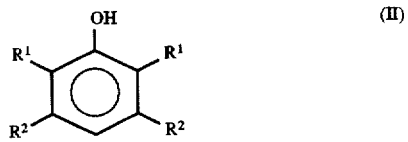

(II)

wherein each $R^1$ and $R^2$ is independently hydrogen, halogen, primary or secondary lower alkyl (i.e., alkyl containing up to 7 carbon atoms), phenyl, or alkyl substituted phenyl, could be utilized in the present invention to make various substituted tris(4-hydroxyphenyl) compounds. Preferably, each $R^2$ independently is hydrogen or primary alkyl. Likewise, 4-hydroxyphenol ketones of Formula (III):

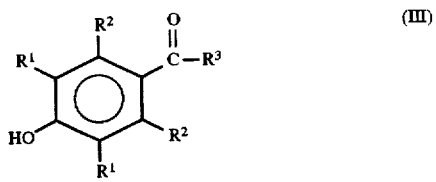

(III)

wherein each $R^1$ and $R^2$ is as previously defined and $R^3$ is a primary or secondary lower alkyl (i.e., alkyl containing up to 7 carbon atoms), phenyl, or alkyl substituted phenyl, could also be utilized. Preferably, each $R^2$ independently is hydrogen or primary alkyl and $R^3$ is an alkyl group. Various combinations are also possible for all the substituents. The resultant substituted tris(4-hydroxyphenyl) compounds would comprise Formula (IV):

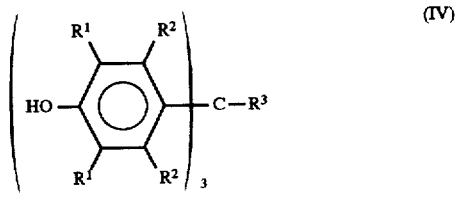

(IV)

wherein each $R^1$, $R^2$, and $R^3$ are as previously defined. The preferred reaction materials are phenol and 4-hydroxyacetophenone for the preparation of THPE.

An illustrative overall reaction scheme for THPE of the present invention can be outlined as follows:

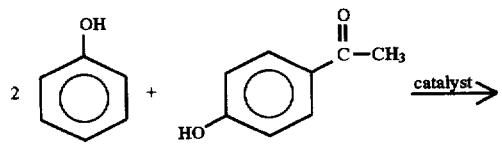

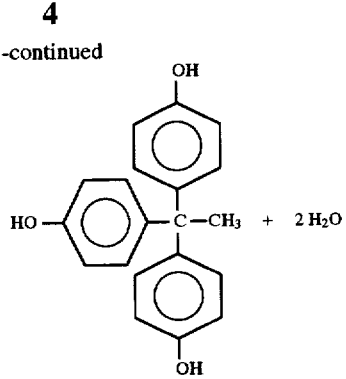

+ 2 H₂O which illustrates the condensation reaction between phenol and 4-hydroxyacetophenone, based on stoichiometric ratios.

The product mixture of the above reaction generally contains THPE, excess phenol and 4-hydroxyacetophenone and water (as a reaction by-product), in addition to any inert solvent or water that was added to the reaction mixture. The THPE is often isolated via filtration and crystallization techniques known to one skilled in the art. Examples of isolation techniques which can be utilized can be found in U.S. Pat. Nos. 4,400,555 (Mendiratta), 4,507,509 (Mendiratta), and 4,992,598 (Strutz et al), which are incorporated herein by reference.

Any ion-exchange resin having appended sulfonic acid groups may be utilized according to the present invention. Some of these are described in U.S. Pat. No. 4,400,555 (Mendiratta), which is incorporated herein by reference. The polymer matrix of the resin itself may be formed of a variety of materials, such as polystyrene; copolymers of styrene and divinylbenzene; acrylic based polymers; phenolic polymers; and Teflon® type materials such as, for example, tetrafluorocarbon or fluorinated ethylene propylene polymers.

Illustrative sulfonated polystyrene resins which can be utilized in the present invention are formed of copolymers of styrene and divinylbenzene, the latter compound generally being employed as a crosslinking agent at a level of about 1% to about 50% by weight, based on the total resin weight. The degree of crosslinking of the polymer enables higher throughput rates in a continuous reaction process by preventing deformation of the ion exchange resin. Specific examples of commercially available sulfonic acid containing ion exchange resins include: resins sold under the tradenames AMBERLITE and AMBERLYST resins, available from Rohm and Haas; DOWEX resins, available from Dow Chemical Company; and LEWATIT BG, available from Bayer.

The resins are generally purified prior to use by means of repeated washing with several volumes of deionized water prior to use. Ion exchange resins that have been treated with repeated washings with base followed with washing with acid as described in U.S. Pat. No. 4,847,432 (Faler), which is incorporated herein by reference, are also useful.

The ion exchange resins can be predried prior to use in the condensation reaction in a standard method such as heating in a dry air stream at elevated temperatures, typically from about 90° C. to about 100° C. The ion exchange resin can also be used in the present invention wet, that is, without a drying step when the water washing step is utilized. When the ion exchange resin is used without a predrying step, the resin can be dehydrated by passing anhydrous solvent, such as anhydrous phenol, through a column containing the wet resin prior to the condensation reaction.

A rate accelerator or co-catalyst is used in a preferred embodiment of the present invention in order to effectively accelerate the condensation reaction. A useful class of accelerators are mercaptans. The mercaptan can be an alkyl mercaptan and can have other non-alkyl moieties present such as, for example, carboxyl. Sometimes a mixture of mercaptans is used. The mercaptan can be present either as a free promoter in the reaction mixture or can be bound to a polymeric resin such as the ion exchange resin. An effective amount of free mercaptan present as a promoter is typically in the range of about 1:20 to 1:1 mole ratio of mercaptan to ketone, although the exact amount utilized is not critical. The ion exchange resins can be partially modified by reacting the acid groups on the resin with mercapto alkyl amines, by partially esterifying the acid resins with a mercapto alcohol, or with an alkyl amine precursor such as thiazolidines. It is sometimes preferred to use a polymer bound mercaptan as a promoter to avoid having the promoter present in the final reaction mixture. Examples of the preparation of polymer bound mercaptan promoters can be found in U.S. Pat. Nos. 4,294,995 (Faler et al), 4,396,728 (Faler) and 4,584,416 (Pressman et al), all of which are incorporated herein by reference.

The unmodified ion exchange resins generally have an ion exchange capacity of at least 2.0 milliequivalents of $H^+$, with exchange capacities in the range of from about 3 milliequivalents of $H^+$ to about 5 milliequivalents of $H^+$; per gram of dry resin. About 5% to about 35% or more, of the acid sites are modified by reacting the acid sites with a mercapto group, for the case when the mercaptan is bound.

The present process for conducting the condensation reaction of phenol and 4-hydroxyacetophenone to form THPE can be carried out in accordance with methods in the art for ion exchange catalyzed condensation reactions. The condensation reaction can be carried out either in a batch mode or in a continuous process. Mole ratios of phenol to 4-hydroxyacetophenone can range from about 4:1 to about 20:1 or an even greater amount of phenol. Substantially anhydrous reaction conditions can be used whereby the water reaction by-product is maintained at less than 2% through the use of anhydrous feed stocks and anhydrous reaction conditions known in the art. Examples of reaction conditions can be found in U.S. Pat. Nos. 4,375,567 (Faler), 4,391,997 (Mendiratta), and 4,590,303 (Mendiratta), all of which are incorporated herein by reference.

Optimum results are obtained for the condensation reaction when the reaction temperature is maintained between about 50° C. and about 90° C. The reaction can be carried out at atmospheric, sub-atmospheric, or super-atmospheric pressures. In general, the reaction is maintained under an inert and preferably, anhydrous atmosphere in the reaction. In a continuous reaction operation, a slightly elevated pressure is preferred to insure adequate flow of the materials through the reaction system.

Removal of at least a portion, preferably a substantial portion, of the water of reaction is preferred to drive the condensation to near completion. This can be accomplished by several methods including sparging the reaction with an inert dry gas such as, for example, dry nitrogen gas, or azeotropic removal of the water with an inert solvent such as, for example, toluene, methylene chloride, 1,2-dichloroethane, or mixtures of solvents capable of forming azeotropes with water. Molecular sieves may also be used to remove the water of reaction. Organic sponges for water such as, for example, anhydrides and ortho esters typically are not preferred as they can also react with the desired phenolic products and/or co-catalyst to result in a reduction in the yield obtained. Organic sponges that would be selective for water but not phenolic compounds and/or the co-catalyst would, however, be useful for the present reaction.

For removal of the water of reaction from the reaction mixture, a sparge of dry inert gas through the reaction solution or ion exchange bed during the reaction is sufficient to remove the water. Various reactor designs are known in the art for both batch and continuous processes for sparging a reactor, collecting the wet effluent by evaporation and distillation followed by returning the dry solvent to the reaction. In a batch reaction mode, the distilled solvent can be recycled into the next batch or added back into the same reaction.

Azeotropic removal of the water of reaction can be achieved in a likewise fashion to sparging the reaction mixture. It is preferable that the azeotropic solvent selected have an azeotropic boiling point lower than the phenol utilized in the condensation reaction in order to prevent unintentional loss of the phenol from the reaction mixture. Phenol can however be utilized for the azeotropic removal of the water of the reaction with replacement of the phenol in order to maintain the level of phenol within the preferred range. It is also preferable that the azeotropic solvent not be reactive towards any of the chemical reagents or the THPE. Mixtures of solvents can also be utilized. Reactor designs are known in the art for both batch and continuous processes to recycle the azeotropic solvent either into the same reaction for continuous removal of water or into a subsequent condensation reaction.

The removal of the water can be done continuously during the condensation reaction or can be done in steps at intervals during the reaction. It is also possible to utilize a single water removal step after the reaction has substantially progressed to further the reaction towards completion. By substantially progressed is meant that the percentage conversion of the starting materials into THPE is at least about 20 mole percent converted.

With respect to the preparation of trisphenols utilizing a sulfonated aromatic organic polymer containing N-alkylaminoorganomercaptan groups as the ion exchange resin, a mixture of phenol and ketone can be heated in the presence of the cation-exchange resin prepared in accordance with the practice of the present invention. There can be utilized 4–20 moles of the phenol per mole of the ketone which can be heated at a temperature in the range of from about 50° C. to about 110° C. with agitation. The ion-exchange resin can be employed at from about 0.1% to about 50% or more by weight, based on the weight of the total mixture in instances where a batch process is used. In a preferred procedure for making trisphenols in a continuous manner, the ion-exchange resin can be used in a column which can be operated at a temperature of about 50° C. to about 100° C. The mole ratio of reactants can vary widely, such as from about 3 to 1 to about 30 to 1 or more, moles of phenol per mole of ketone. It is preferred, however, to use the reactants at a mole ratio of about 5 to 1 to about 20 to 1 moles of phenol per mole of ketone. The impurities present in the reaction mixture are generally less than 30%, preferably less that 20% and most preferably less than 10%; wherein the % by area of the impurities was determined by liquid chromatography analysis using 254 nm UV detector (% impurities area of the impurities times 100 divided by the sum of the area of the impurities and the area of the THPE). The color bodies can be detected by UV spectroscopy in methanol at 0.2 grams/10 mL. The absorbance of the THPE as precipitated from the reaction mixture measured at 422, 500, and 600 nm is generally less than 0.1, 0.1, and 0.1; preferable less than about 0.1, 0.01, and 0.05; and most preferably less than about 0.06, 0.03, and 0.01, respectively.

One method of recovering the trisphenol reaction product, for example, THPE, is by crystallizing the trisphenol reaction product from the reactor effluent. Another procedure involves the partial distillation to remove the phenol followed by recrystallization of the residual trisphenol using methanol, methanol/water, ethanol, ethanol/water, 2-propanol, 2-propanol/water, phenol, phenol/methylene chloride, or phenol/1,2-dichloroethane as the solvent. A crystallization procedure for BPA recovery is also shown in U. S. Pat No. 4,375,567 (Faler), which is incorporated herein by reference, is also useful for recovering THPE and other trisphenols. If desired, in addition to, or instead of recrystallization, the crude trisphenol reaction product solution or the trisphenol dissolved in a suitable solvent can be treated with activated carbon or a sodium borohydride solution as illustrated by U.S. Pat. No. 4,992,598 (Strutz, et al).

For another embodiment of the present invention, the trisphenol reaction mixture can be admixed with a non-solvent for the trisphenol to cause the trisphenol to precipitate from the reaction solution. It is preferred that the starting materials as well as the reaction impurities be soluble in the non-solvent for the trisphenol. It is also preferred that the non-solvent and the starting materials be readily separable from each other such that the starting materials could be recycled into subsequent trisphenol synthesis reactions. Non-limiting examples for the non-solvent include both halogenated and non-halogenated lower alkyl and aryl solvents. Preferred non-solvents include, for example, 1,2-dichloroethane, dichloromethane, toluene, and xylene. Especially preferred are the lower alkyl halogenated solvents, including 1,2-dichloroethane, dichloromethane.

The branched polycarbonates comprise structural units of the formula (V):

(V)

wherein $R^3$ is a mixture of divalent organic radicals and trivalent organic radicals.

Suitable $R^3$ values in formula (V) include ethylene, propylene, trimethylene, tetramethylene, hexamethylene, dodecamethylene, 1,4-(2-butenylene), 1,10-(2-ethyldecylene), 1,3-cyclopentylene, 1,3-cyclohexylene, 1,4-cyclohexylene, m-phenylene, benzene-1,4-dimethylene (which is a vinylog of the ethylene radical and has similar properties) and similar radicals such as those which correspond to the dihydroxy compounds disclosed by name or formula (generic or specific) in U.S. Pat. No. 4,217,438, the disclosure of which is incorporated by reference herein. Also included are radicals containing non-hydrocarbon moieties. These may be substituents such as chloro, nitro, alkoxy and the like, and also linking radicals such as thio, sulfoxy, sulfone, ester, amide, ether and carbonyl. Most often, however, all $R^3$ radicals are hydrocarbon radicals.

Preferably at least about 60% and more preferably at least about 80% of the total number of $R^3$ values in the cyclic oligomer mixtures, and most desirably all of said $R^3$ values, are aromatic. The aromatic $R^3$ radicals preferable include those having the formula (VI):

(VI)

wherein each of $A^1$ and $A^2$ is a monocyclic divalent aromatic radical and Y is a bridging radical in which one or two atoms separate $A^1$ form $A^2$. The free valence bonds in formula (VI) are usually in the meta or para positions of $A^1$ and $A^2$ in relation to Y.

In formula (VI), the $A^1$ and $A^2$ values may be unsubstituted phenylene or substituted derivatives there of, illustrative substituents (one or more) being alkyl, alkenyl, halo (especially chloro and/or bromo), nitro, alkoxy and the like. Unsubstituted phenylene radicals are preferred. Both $A^1$ and $A^2$ are preferable p-phenylene, although both may be o- or m-phenylene or one o- or m-phenylene and the other p-phenylene.

The bridging radical, Y, is one in which one or two atoms, preferable one, separate $A^1$ from $A^2$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gem-alkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone. For reasons of availability and particular suitability for the purposes of this invention, the preferred radical of formula (VI) is the 2,2-bis(4-phenylene)propane radical, which is derived from bisphenol A and in which Y is isopropylidene and $A^1$ and $A^2$ are each p-phenylene.

In the present invention, the polycarbonate comprises $R^3$ radicals comprising divalent radials of formula (VI) and trivalent radicals of formula (IV), as previously described. The preferred divalent radials are derived from bisphenol A and the preferred trivalent radicals are derived from THPE. The preferred ranges of di to tri-valent radicals is from about 100–500:1, the more preferred range is from about 150–400:1 and the most preferred range is from about 200–340:1 ; based on a mole to mole ratio. The exact ratio of monomers is determined by the ultimate properties that are desired in the final branched polymeric resin.

The polycarbonates of the present invention can be prepared by the reaction of a bisphenols/trisphenols mixture with a carbonic acid source. The bisphenols/trisphenols mixture are as previously described and the carbonic acid source can be phosgene or diphenyl carbonate. Polycarbonates can be prepared by a transesterification process utilizing aromatic diesters of carbonic acid in the presence of basic catalysts with the bisphenols/trisphenols mixture to give high molecular weight polycarbonates. Solution polymerization processes can be used which comprise phosgenation of the bisphenols/trisphenols mixture in a mixture of a chlorinated hydrocarbon and a base, for example, pyridine are known. Interfacial polymerization can also be utilized which comprises phosgenation of sodium salts of the bisphenols/trisphenols mixture in an aqueous alkaline solution or as a suspension in an inert organic solvent. Phosgene free synthetic routes utilizing carbon monoxide with the aid of catalysts can also be used. Polymerization of macrocyclic polycarbonates can also be used to make higher molecular weight polycarbonates of the present invention.

All patents cited by reference are incorporated by reference herein.

In order that those skilled in the art will be better able to practice the invention, the following examples are given by way of illustration and not by way of limitation.

EXAMPLES

The following are examples of the formation of THPE using an ion exchange catalyst.

Catalyst preparation

The ion exchange catalyst was prepared as follows:

1. The resin was washed in a Buchner funnel with several volumes of deionized water until the filtrate was colorless. Then, the majority of the water was removed by washing the resin with methanol.

Example 1

Preparation of THPE

A mixture of 94 g (1.0 mol) of phenol, 5.31 g (0.0500 mol) of 3 mercaptopropionic acid, 10 g of Lewatit BG ion exchange resin and 1.0 g of 2,6-dimethylnaphthalene (internal standard for liquid chromatography analysis) was heated under a static nitrogen atmosphere to 65° C. in a round bottom flask equipped with a condenser, an internal thermometer and a mechanical stirrer. To this mixture was added 11.35 g (0.08336 mol) of 4-hydroxyacetophenone. The mixture was stirred with heating while samples were obtained periodically. Three to four drops of the reaction solution was added to 10 mL of acetonitrile for liquid chromatography analyses. After about 8 hrs., the reaction mixture was separated from the ion exchange resin by filtration and the THPE was isolated by the addition of methylene chloride (about 400 mL). The results monitoring reaction completion versus Comparative Example 1 are found in Table I. The THPE was washed with additional methylene chloride and dried. To determine the level of color bodies, 0.2 grams of THPE was dissolved in 10 mL of methanol and the UV absorption was measured at 422, 500, and 600 nm. The results measured at different wavelengths can be found in Table II.

Comparative Example 1

The following is an example of the preparation of THPE using HCl. A solution of 94 g (1.0 mol) of phenol, 1.2 g (0.011 mol) of 3 mercaptopropionic acid and 0.1 g of 2,6-dimethylnaphthalene was heated to 65° C. in a round bottom flask equipped with a condenser, an internal thermometer, a HCl dip tube and a mechanical stirrer. Dry HCl gas was bubbled into the solution for 1 hr to ensure that the solution was saturated with HCl. To this mixture was added 11.35 g (0.08336 mol) of 4-hydroxyacetophenone. The mixture was stirred with heating while samples were obtained periodically. Three to four drop of the reaction solution was added to 10 mL of acetonitrile for liquid chromatography analyses. After about 8 hrs., the reaction mixture was separated from the ion exchange resin by filtration and the THPE was isolated by the addition of methylene chloride (about 400 mL). The THPE was washed with additional methylene chloride and dried. To determine the level of color bodies, 0.2 grams of the washed THPE was dissolved in 10 mL of methanol and the UV absorption was measured at 422, 500, and 600 nm. (note Table II for color body data.)

TABLE I

Composition of THPE Reaction Products With Time (a)

| Reaction time (hrs) | Example 1 % THPE (b) | Example 1 % Impurities (c) | Comparative Example 1 % THPE (b) | Comparative Example 1 % Impurities (c) |
| --- | --- | --- | --- | --- |
| 1 | 81 | 19 | 19 | 81 |
| 2 | 91 | 9 | 18 | 82 |
| 4 | 93 | 7 | 22 | 78 |
| 6 | 92 | 8 | 34 | 66 |
| 8 | 90 | 10 | 33 | 67 | a. Results obtained on a LC using a UV detector at 254 nm.
b. % THPE = 100 × area from THPE peak divided by the sum of the areas of the THPE and impurities peaks
c. % impurities = 100 × area from impurities peaks divided by the sum of the areas of the THPE and impurities peaks

Example 2

Preparation of THPE in a continuous reactor

To a jacketed reactor containing 398 grams of Lewatit BG ion exchange resin at about 65° C. was fed a solution of 1500 grams (15.9 moles) of phenol, 181.12 grams (1.33 moles) of 4-hydroxyacetophenone and 2.7 grams (0.025 moles) of 3-mercapropionic acid at 0.7 grams/minute. About 3 to 4 drops of reaction product was dissolved in 10 mL of acetonitrile for liquid chromatography (LC) analysis. By LC, the THPE was about 76% of the reaction products and the impurities were about 24% (as defined in Table I). The reaction product was precipitated into methylene chloride (about 4 mL of methylene chloride/grams of reaction product). The THPE was isolated by filtration, washed with methylene chloride and dried. To determine the level of color bodies, 0.2 grams of the THPE reaction product was dissolved in 10 mL of methanol and the UV absorbance was obtained at 422, 500 and 600 nm. These results measured at different wavelengths can also be found in Table II.

TABLE II

Absorbance of THPE Reaction Products (a)

| Wavelength (nm) | Example 1 | Example 2 | Comparative Example 1 |
| --- | --- | --- | --- |
| 422 | 0.055 | 0.044 | 1.710 |
| 500 | 0.027 | 0.024 | 0.457 |
| 600 | 0.010 | 0.010 | 0.201 | a. The THPE reaction products (0.2 grams) were dissolved in 10 mL of methanol.

Liquid chromatographic analyses were performed on the samples obtained from the reaction mixtures using standard chromatographic techniques known to one skilled in the art. Analyses of the HCl catalyzed reaction revealed the presence of both the phenol and 4-hydroxyacetophenone starting materials and THPE. As indicated by the data in Table I, there was an impurity that persisted to be present in the reaction mixture, irrespective of the length of the reaction time. By comparison, analyses of the samples from the ion exchange resin catalyzed reaction revealed the presence of both the phenol and 4-hydroxyacetophenone starting materials and THPE, however, surprisingly, the impurities found in the ion-exchange catalyzed reaction were at dramatically lower levels throughout the reaction time. As noted in Table II, the level of the color bodies in the final product were unexpectedly greatly reduced as shown by the lower absorbance levels obtained at 422 to 600 nm. The reduced level of color bodies translates into a lower level of color in the final product.

Example 3

Preparation of THPE Using an ion exchange catalyst and a nitrogen sparge to remove water A mixture of 94 grams (1.0 mol) of phenol, 5.31 g (0.0500 mol) of 3-mercaptopropionic acid, 10 g of LEWATIT BE ion exchange resin and 1.0 g of 2,6-dimethylnaphthalene (internal standard for liquid chromatography analysis) was heated to about 65° C. in a round bottom flack equipped with a distillation setup, an internal thermometer and a mechanical stirrer. The solution was continuously sparged with nitrogen (using a dip tube) to remove the water. To this mixture was added 11.35 g (0.8336 mol) of 4-hydroxyacetophenone. The mixture was stirred at about 65° C with the nitrogen sparge for about 8 hrs. The THPE was isolated by precipitation with methylene chloride (4 mL/1 g of reaction mixture) and the yield is given in Table III.

Comparative Example 2

Preparation of THPE Using an ion exchange catalyst with no water removal

A mixture of 94 grams (1.0 mol) of phenol, 5.31 g (0.0500 mol) of 3-mercaptopropionic acid, 10 g of LEWATIT BE ion exchange resin and 1.0 g of 2,6-dimethylnaphthalene (internal standard for liquid chromatography analysis) was heated to about 65° C. in a round bottom flask equipped with a condenser, an internal thermometer and a mechanical stirrer. The solution was held under a static nitrogen atmosphere and stirred at about 65° C. for about 8 hrs. after which the THPE was isolated by precipitation with methylene chloride (4 mL/1 g of reaction mixture). The yield is given in Table III.

Comparative Example 3

Preparation of THPE Using an ion exchange catalysts with no water removal

A mixture of 94 grams (1.0 mol) of phenol, 5.31 g (0.0500 mol) of 3-mercaptopropionic acid, 8.5 g (0.083 mol) of acetic anhydride, 10 g of LEWATIT BE ion exchange resin and 1.0 g of 2,6-dimethylnaphthalene (internal standard for liquid chromatography analysis) was heated to about 65° C. in a round bottom flack equipped with a condenser, an internal thermometer and a mechanical stirrer. The solution was held under a static nitrogen atmosphere and to this mixture was added 11.35 g (0.8336 mol) of 4-hydroxyacetophenone. The mixture was stirred at about 65° C. for about 8 hrs after which the THPE was isolated by precipitation with methylene chloride (4 mL/1 g of reaction mixture). The yield is given in Table III.

Comparative Example 4

Preparation of THPE Using an ion exchange catalyst with no water removal

A mixture of 94 grams (1.0 mol) of phenol, 5.31 g (0.0500 mol) of 3-mercaptopropionic acid, 10 g (0.083 mol) of trimethyl orthoacetate, 10 g of LEWATIT BE ion exchange resin and 1.0 g of 2,6-dimethylnaphthalene (internal standard for liquid chromatography analysis) was heated to about 65° C. in a round bottom flack equipped with a condenser, an internal thermometer and a mechanical stirrer. The solution was held under a static nitrogen atmosphere and to this mixture was added 11.35 g (0.8336 mol) of 4-hydroxyacetophenone. The mixture was stirred at about 65° C. for about 8 hrs following which the THPE was isolated by precipitation with methylene chloride (4 mL/1 g of reaction mixture). The yield is given in Table III.

Comparative Examples 3 and 4 show that typical methods used to remove or react with water using an orthoester or an anhydride as organic sponges did not lead to satisfactory results.

TABLE III

Preparation of THPE Using Ion Exchange With and Without Various Methods Of Water Removal

| | Comparative Example 2 | Example 3 | Comparative Example 3 | Comparative Example 4 |
| --- | --- | --- | --- | --- |
| Method of Water Removal | None | Nitrogen Sparge | Acetic Anhydride | Trimethylortho acetate |
| % Yield | 25 | 48 | 24 | 16 |

Comparative Example 5

Preparation of THPE Using HCl gas

A mixture of 10 grams (0.11 mol) of phenol, 0.12 g (0.0012 mol) of 3-mercaptopropionic acid and 0.1 g of 2,6-dimethylnaphthalene (internal standard for liquid chromatography analysis) was heated to about 55° C. in a round bottom flask equipped with a condenser, an internal thermometer, a dip tube and a magnetic stirrer. The solution was saturated with dry HCl gas for about 3 hrs followed by the addition of 1.2 g (0.0088 mol) of 4-hydroxyacetophenone. The mixture was stirred at about 55° C. for about 12 hrs while the HCl addition was continued. Three to four drops of the reaction mixture was removed with time over the course of the reaction, diluted with acetonitrile and used for liquid chromatography. The yield over time is given in Table IV.

Example 4

Preparation of THPE Using HCl gas and the Water/ 1,2-Dichloroethane (EDC) Azeotrope to Remove Water A mixture of 10 grams (0.11 mol) of phenol, 0.12 g (0.0012 mol) of 3-mercaptopropionic acid and 0.1 g of 2,6-dimethylnaphthalene (internal standard for liquid chromatography analysis) was heated to about 55° C. in a round bottom flask equipped with a condenser, an internal thermometer, a dip tube and a magnetic stirrer. The solution was saturated with dry HCl gas for about 3 hrs followed by the addition of 1.2 g (0.0088 mol) of 4-hydroxyacetophenone. The mixture was stirred at about 55° C. while HCl addition was continued. After about 7 hrs, 6.3 mL of EDC was added and vacuum was applied to remove the water/EDC azeotrope over about 1.5 hrs. The HCl was added to continue the reaction for an about an additional 3.5 hrs. Three to four drops of the reaction mixture was removed with time over the course of the reaction, diluted with acetonitrile and used for liquid chromatography. The yield over time is given in Table IV.

Example 5

Preparation of THPE Using HCl gas and the Water/ Phenol azeotrope to Remove Water A mixture of 200 grams (2.13 mol) of phenol, 1.51 g (0.0142 mol) of 3-mercaptopropionic acid was heated to about 50° C. in a round bottom flask equipped with a condenser, an internal thermometer, a dip tube and a mechanical stirrer. The solution was saturated with dry HCl gas followed by the addition of 12.1 g (0.0890 mol) of 4-hydroxyacetophenone and 1.0 g of 2,6-dimethylnaphthalene (internal standard for liquid chromatography analysis). The mixture was stirred at about 55° C. and after about 6 hrs, a vacuum was applied to remove the water/phenol azeotrope over about 1.25 hrs. Then, HCl was added to the reaction for about 10 hrs (overnight). The reaction was continued for about an additional 3.5 hrs. Three to four drops of the reaction mixture was removed with time over the course of the reaction, diluted with acetonitrile and used for liquid chromatography. The yield over time is given in Table IV.

TABLE IV

Preparation of THPE Using HCl Gas With and Without Water Removal

| Reaction Time (hrs) | Comparative Example 5[a] | Example 4[a] | Example 5[a] |
|---|---|---|---|
| 2 | 32 | | |
| 4 | 41 | | |
| 6 | 52 | 50 | 17[c] |
| 7 | | 56[b] | |
| 7.25 | | | 57 |
| 12 | 68 | 98 | |
| 17.25 | | | 84 |
| 20.75 | | | 89 |

[a] % yield determined by LC.
[b] EDC was added after the 7th hour sample and then distilled out to remove the water of reaction.
[c] After the 6th hour sample, vacuum was applied to distill out the water as the phenol/water azeotrope.

As noted by the data in Table IV, removal of the water from an acid catalyzed condensation reaction leads to an extremely high conversion to THPE.

Comparative Examples for the Preparation of Bis-Phenols

The following experiments demonstrate the results for water removal for bis-phenol condensation reactions. The bis-phenol reactions were carried with and without a nitrogen sparge to remove the water of reaction (Table V). As demonstrated by these data, in the case of bis-phenol condensations, there is no advantage in removing the water of reaction. One skilled in the art would expect from this data that there would be no benefit in removing the water from general trisphenol condensation reactions, and in particular, the THPE condensation reactions.

Comparative Example 6

Preparation of BPA Without Water Removal

A mixture of 112.8 grams (1.19 mol.) of phenol, and 12 g of Lewatit BG ion exchange resin was heated to about 65° C. in a round bottom flask equipped with a condenser, an internal thermometer and a mechanical stirrer followed by the addition of 0.048 g (400 ppm) of 3-mercaptopropionic acid and 5.8 gram (0.10 mol) of acetone. The solution was stirred under a static nitrogen atmosphere and the progress of the reaction was followed with time by LC analysis on samples removed with time (Table V).

Comparative Example 7

Preparation of BPA With The Removal Of Water

A mixture of 112.8 grams (1.19 mol) of phenol, and 12 g of Lewatit BG ion exchange resin was heated to about 65° C. in a round bottom flask equipped with a condenser, an internal thermometer and a mechanical stirrer followed by the addition of 0.048 g (400 ppm) of 3-mercaptopropionic acid and 5.8 gram (0.10 mol) of acetone. The solution was stirred while nitrogen was sparged through the mixture to remove the water of reaction. The progress of the reaction was followed with time by LC analysis on samples removed with time (Table V).

TABLE V

Preparation Of Bisphenol A With and Without The Removal Of Water Using A Nitrogen Sparge (a.).

| | Wt % BPA In Reaction Mixture | |
|---|---|---|
| Reaction Time (hrs) | Comparative Examples 6 Static Nitrogen | Comparative Example 7 Nitrogen Sparge |
| 1.0 | 9.1 | 6.0 |
| 1.5 | 10.2 | 8.7 |
| 2.2 | 11.5 | 10.1 |
| 2.5 | 12.2 | 11.3 |
| 3.1 | | 12.2 |

As seen by the data in Table V, removal of the water of reaction for bisphenol preparation does not lead to an increased yield of the bisphenol. In the experiments illustrated above, the nitrogen sparge to remove the water of reaction (Comparative Example 7) showed no observed improvement in the conversion as compared to the control without the sparge (Comparative Example 6). From these illustrative data for the preparation of bisphenol it would be expected that THPE would likewise show no improvement in yield for reactions in which the water of reaction is removed.

Example 6

Isolation of THPE prepared by an HCl process

THPE was prepared by the reaction of 940 grams (10 mol) of phenol, 1.6 grams (0.015 mol) of 3-mercaptopropionic acid and 113.5 g (0.883 mol) of 4-hydroxyacetophenone at 65° C. using HCl gas. Portions of the phenol/THPE mixture was added to the solvents listed in Table VI at 0.25 grams of reaction mixture per mL of solvent. After 24 hrs, the presence of a precipitate was recorded and the product was isolated, washed with the solvent used for precipitation, and dried. The yields were recorded in grams product/gram of reaction mixture. To determine the level of color bodies, 0.2 grams of THPE was dissolved in 10 mL of methanol and the UV absorption was measured at 422, 500, and 600 nm.

TABLE VI

Isolation of THPE by Precipitation.

| Precipitation Solvent (a.) | Yield (b.) | Product absorbance (c.) | | |
|---|---|---|---|---|
| | | 422 nm | 500 nm | 600 nm |
| acetonitrile | no ppt. | | | |
| water | no ppt. | | | |
| IPA | no ppt. | | | |
| MEOH | no ppt. | | | |
| EDC | 0.0744 | 1.17 | 0.267 | 0.0622 |
| MeCl$_2$ | 0.0803 | 1.1473 | 0.26228 | 0.071 |
| 70/30 MeOH/H$_2$O | no ppt. | | | |
| CCl$_4$ | 0.0744 | 3.619 | 1.397 | 0.26105 |
| Heptane | 3 phases | | | |

TABLE VI-continued

Isolation of THPE by Precipitation.

| Precipitation Solvent (a.) | Yield (b.) | Product absorbance (c.) | | |
|---|---|---|---|---|
| | | 422 nm | 500 nm | 600 nm |
| DMF | no ppt. | | | |
| THF | no ppt. | | | |
| 73/30 H₂O/MeOH | no ppt. | | | |
| CHCl₃ | 0.0688 | 1.3375 | 0.30652 | 0.08853 |
| chlorobenzene | 0.0797 | 2.01122 | 0.58212 | 0.15343 | a. Reaction effluent/precipitation solvent = 0.25 grams/mL.
b. Yield in grams of product per grams of reaction effluent.
c. By UV-Vis at indicated wavelength (0.20 grams product/10 mL of methanol).

In a second experiment, a mixture of 94 grams (1.0 mol) of phenol, 2.83 (0.027 mol) of 3-mercaptopropionic acid and 1.0 g of 2,6-dimethylnaphthalene (an internal standard for liquid chromatography analysis) was heated to about 45° C. in a round bottom flask equipped with a condenser, an internal thermometer, a dip tube and a magnetic stirrer. The solution was saturated with dry HCl gas for about 0.5 hours followed by the addition of 22.69 g (0.166 mol) of 4-hydroxyacetophenone. The mixture was stirred at about 45° C. for about 8 hours while the HCl addition was continued. Portions of the reaction mixture were removed and precipitated into the solvents listed in Table VII at 1 mL of reaction mixture/4 mL of precipitation solvent. After about 24 hours, the product was isolated, washed with the precipitation solvent, and dried. The yields were recorded in grams product/mL of reaction mixture. To determine the level of color bodies, 0.2 grams of THPE was dissolved in 10 mL of methanol and the UV absorption was measured at 422, 500, and 600 nm.

TABLE VII

Isolation of THPE by Precipitation

| Precipitation solvent (a.) | Yield (b.) | Product absorbance (c.) | | |
|---|---|---|---|---|
| | | 422 nm | 500 nm | 600 nm |
| Toluene | 0.2950 | 3.93 | 3.88 | 0.56 |
| EDC | 0.2480 | 1.07 | 0.41 | 0.06 |
| MeCl₂ | 0.2370 | 1.17 | 0.56 | 0.05 | a. Reaction effluent/precipitation solvent = 0.25 mL/mL.
b. Yield in grams of product per mL of reaction effluent.
c. By UV-Vis at indicated wavelength (0.20 grams product/10 mL of methanol).

Example 7

Isolation Of THPE prepared by the Ion Exchange Resin process

In another experiment, a mixture of 94 grams (1.0 mol) of phenol 5.31 g 0.0500 mol) of 3-mercaptopropionic acid, 10 g of Lewatit BG ion exchange resin and 1.0 g of 2,6-dimethylnaphthalene (an internal standard for liquid chromatography analysis) was heated to about 65° C. in a round bottom flask equipped with a distillation setup, an internal thermometer and a mechanical stirrer. The solution was continuously sparged with nitrogen (using a dip tube) to remove the water to this mixture was added 11.35 g (0.8336 mol) of 4-hydroxyacetophenone. The mixture was stirred at about 65° C. with the nitrogen sparge for about 8 hours followed by isolation of the THPE via precipitation in the solvents listed in Table VIII (1 mL of reaction mixture/4 mL). After 24 hours the product was isolated, washed with the precipitation solvent, and dried. The yields were recorded in grams product/mL of reaction mixture. To determine the level of color bodies, 0.2 grams of THPE was dissolved in 10 mL of methanol and the UV absorption was measured at 422, 500 and 600 nm.

TABLE VIII

Isolation of THPE by Precipitation

| Precipitation solvent (a.) | Yield (b.) | Product absorbance (c.) | | |
|---|---|---|---|---|
| | | 422 nm | 500 nm | 600 nm |
| Toluene | 0.2469 | 0.32 | 0.14 | 0.04 |
| EDC (d.) | 0.2322 | 0.32 | 0.13 | 0.03 |
| MeCl₂ | 0.2408 | 0.32 | 0.15 | 0.04 | a. Reaction effluent/precipitation solvent = 0.25 mL/mL.
b. Yield in grams of product per mL of reaction effluent.
c. By UV-Vis at indicated wavelength (0.20 grams product/10 mL of methanol).
d. EDC is 1,2-dichloroethane.

These results illustrate that chlorinated solvents and aromatic solvents are useful in the separation of THPE from the phenol of THPE. The most preferred precipitation solvents are those that afford the lowest color THPE with the highest isolated yields (methylene chloride and EDC).

What is claimed:

1. A method of making a tris(4-hydroxyphenyl) compound of the formula:

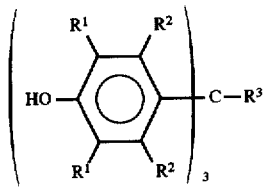

which comprises heating a mixture comprising a phenol species of the formula:

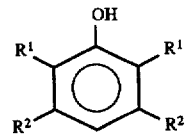

and a hydroxyphenyl ketone material of the formula:

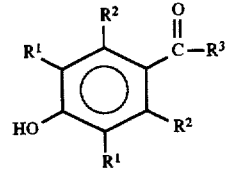

wherein each $R^1$ and $R^2$ is independently hydrogen, halogen, primary or secondary lower alkyl having from 1 to about 7 carbon atoms, phenyl, or alkyl substituted phenyl and $R^3$ is a primary or secondary lower alkyl having from 1 to about 7 carbon atoms, phenyl, or alkyl substituted phenyl in the presence of an ion exchange catalyst and at least one mercaptan.

2. The method of claim 1 wherein the tris(4-hydroxyphenyl) compound comprises less than about 20% reaction impurities as determined by liquid chromatography at a detector wavelength of 254 nm wherein percent reaction impurities is calculated as 100 times the area from impurities peaks divided by the sum of the areas of the tris(4-hydroxyphenyl) compound and impurities peaks.

3. The method of claim 2 wherein the tris(4-hydroxyphenyl) compound comprises about 10% or less reaction impurities.

4. The method of claim 1, wherein the absorbance of the tris(4-hydroxyphenyl) compound measured at 422, 500, and 600 nm is less than 0.1, 0.1, and 0.1, respectively.

5. The method of claim 1, wherein the absorbance of the tris(4-hydroxyphenyl) compound measured at 422, 500, and 600 nm is less than 0.1, 0.1, and 0.05, respectively.

6. The method of claim 1, wherein the absorbance of the tris(4-hydroxyphenyl) compound measured at 422, 500, and 600 nm is less than about 0.06, 0.03, and 0.01, respectively.

7. The method of claim 1 wherein the mercaptan is polymer bound.

8. The method of claim 7 wherein the ion exchange resin is made from a polymer selected from the group consisting of polystyrene, copolymers of styrene and divinylbenzene, acrylic based polymers, phenolic polymers, tetrafluorocarbon and fluorinated ethylene propylene polymers.

9. The method of claim 1 wherein the ion exchange resin contains sulfonic acid groups.

10. The method of claim 1 wherein the phenol species is phenol and the hydroxyphenyl ketone material is 4-hydroxyacetophenone.

11. The method of claim 10 wherein the mole ratio of phenol to 4-hydroxyacetophenone is at least 2:1.

12. The method of claim 1 wherein the tris(4-hydroxyphenyl) compound is isolated with the use of a chlorinated aliphatic solvent, chlorinated aromatic solvent, or an aromatic solvent.

13. The method of claim 1 which consists essentially of heating a mixture comprising a phenol species and a hydroxyphenyl ketone material in the presence of an ion exchange catalyst and at least one mercaptan, optionally with the removal of the water of reaction.

14. The method of claim 13 wherein the ion exchange resin contains sulfonic acid groups.

15. The method of claim 17 wherein the mercaptan is polymer bound.

16. A method of manufacturing a branched polycarbonate, wherein the method comprises the reaction of (a) a bisphenol, (b) a tris(4-hydroxyphenyl) compound of the formula:

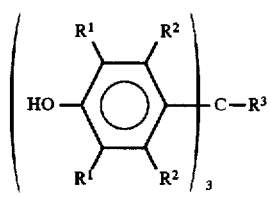

wherein tris(4-hydroxyphenyl) compound is made by a method comprising heating a mixture comprising a phenol species of the formula:

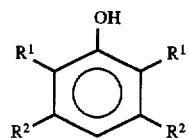

and a hydroxyphenyl ketone material of the formula:

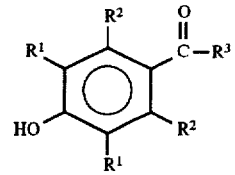

wherein each $R^1$ and $R^2$ is independently hydrogen, halogen, primary or secondary lower alkyl having from 1 to about 7 carbon atoms, phenyl, or alkyl substituted phenyl and $R^3$ is a primary or secondary lower alkyl having from 1 to about 7 carbon atoms, phenyl, or alkyl substituted phenyl in the presence of an ion exchange catalyst and at least one mercaptan; and (c) a carbonic acid source.

17. A method of making a tris(4-hydroxyphenyl) compound of the formula:

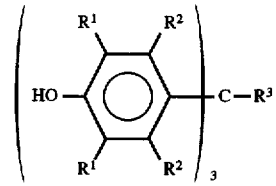

which comprises heating a mixture comprising a phenol species of the formula:

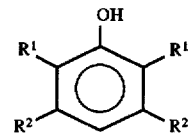

and a hydroxyphenyl ketone material of the formula:

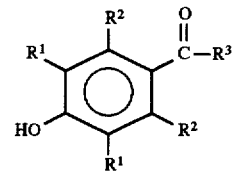

wherein each $R^1$ and $R^2$ is independently hydrogen, halogen, primary or secondary lower alkyl having from 1 to about 7 carbon atoms, phenyl, or alkyl substituted phenyl and $R^3$ is a primary or secondary lower alkyl having from 1 to about 7 carbon atoms, phenyl, or alkyl substituted phenyl in the presence of an acid catalyst wherein the water of reaction is removed from the reaction mixture.

* * * * *